(12) United States Patent
Bukhary

(10) Patent No.: US 8,209,876 B2
(45) Date of Patent: Jul. 3, 2012

(54) DEVICE AND METHOD FOR MEASURING THE SKELETAL DENTAL RELATIONSHIPS

(75) Inventor: Mohammed Taher Bukhary, Riyadh (SA)

(73) Assignee: King Saud University, Riyadh (SA)

( * ) Notice: Subject to any disclaimer, the term of this patent is extended or adjusted under 35 U.S.C. 154(b) by 17 days.

(21) Appl. No.: 12/896,963

(22) Filed: Oct. 4, 2010

(65) Prior Publication Data

US 2012/0079732 A1    Apr. 5, 2012

(51) Int. Cl.
*A61C 19/045*  (2006.01)
*A61B 6/14*  (2006.01)
*B43L 13/20*  (2006.01)
*G01B 11/28*  (2006.01)

(52) U.S. Cl. .......................................... 33/513; 33/563

(58) Field of Classification Search .................... 33/513, 33/563, 565
See application file for complete search history.

(56) References Cited

U.S. PATENT DOCUMENTS

| | | | | |
|---|---|---|---|---|
| 1,899,318 A * | 2/1933 | Dixon | | 434/211 |
| D140,152 S * | 1/1945 | Aichele | | D10/62 |
| 4,279,259 A * | 7/1981 | Lee et al. | | 600/587 |
| 4,630,375 A * | 12/1986 | Spolyar | | 33/1 B |
| 5,278,756 A * | 1/1994 | Lemchen et al. | | 600/587 |
| 5,318,441 A * | 6/1994 | Keller | | 433/68 |
| 5,342,202 A * | 8/1994 | Deshayes | | 434/270 |
| 5,426,859 A * | 6/1995 | Concari et al. | | 33/27.02 |
| 5,724,746 A | 3/1998 | Mack | | |
| 5,950,320 A * | 9/1999 | Dorsey | | 33/512 |
| 6,158,135 A * | 12/2000 | Rank | | 33/494 |
| 6,879,712 B2 | 4/2005 | Tuncay | | |
| 2002/0032449 A1 | 3/2002 | Rota | | |
| 2010/0229413 A1* | 9/2010 | Polei | | 33/514 |
| 2011/0195373 A1* | 8/2011 | Waugh | | 433/24 |

FOREIGN PATENT DOCUMENTS

GB    2374015 A  * 10/2002

* cited by examiner

*Primary Examiner* — Christopher Fulton
(74) *Attorney, Agent, or Firm* — Lowe Hauptman Ham & Berner, LLP

(57) ABSTRACT

A device for measuring the skeletodental relationship of a human skull directly from a cephalometric radiograph or from a hand tracing of the craniofacial structures includes a flat transparent plate-like structure. The plate-like structure has a generally rectangular shape with a zero point and two protractors spaced one below the other and superimposed on a zero point. The protractors include radial lines from 0° to 90° for a first of the protractors and from 90° to 0° for a second of the protractors. Further, the 0° line in the first protractor is parallel with the 90° line in the second protractor. The 0° line in the second is parallel with the 90° line in the first. Further, three vertical scales are provided on the right hand edge and top of the device with two of the scales on the right hand edge, but ascending in different directions.

3 Claims, 5 Drawing Sheets

DEVICE AND METHOD FOR MEASURING THE SKELETAL DENTAL RELATIONSHIPS

FIELD OF THE INVENTION

The present invention relates to a device and a method for measuring the skeletal dental relationships of a human skull directly from a cephalometric radiograph of the craniofacial structure and more particularly to a device and/or method for facilitating the work of dentists, dental students, othrodontists, and researchers interested in studying dental malocclusions and assessing treatments and planing.

BACKGROUND OF THE INVENTION

Apparatus for gauging and determining special coordinates for a source of radiation to be employed in obtaining a radiograph of a patient are well known and have been in use for over 20 years. For example, a U.S. Pat. No. 4,630,375 of Spolyar discloses a template-like gauge having a plate-like body which is at least in most part transparent and carries a reference point and a first plurality of parallel lines along with a read-out portion. The read out portion is made up of second and third pluralities of lines to cooperatively define a plurality of gauge areas. Each of the gauge areas represents a different set of coordinates for aiming an associated X-ray source. An additional plurality of radiating angularly spaced gauge lines are also provided. When a plate-like body is placed against a lateral cephalogram and the reference point is situated at the articulare and the palatal plane of the cephalogram it is positioned at least parallel to one of the lines in the first plurality of parallel lines, the sella appears in one of the gauging areas and the coordinates corresponding thereto are employed for aiming the X-ray source.

A method and apparatus for generating cephalometric images is also well known. For example, a U.S. Pat. No. 5,278,756 of Lemchen et al. discloses a method and apparatus for generating a cephalometric tracing directly from a patient by directly generating digitized two or three dimensional data from the patient's head to define locations of preselected landmarks thereon from which diagnostic data points required for the cephalometric tracing are computer generated and connected so as to produce a cephalometric tracing. A video recording of the patient's head corresponding to the spatial orientation of the cephalometric tracing at the time of the generation of the data is made, reproduced in visible form to the same scale as the cephalometric tracing and superimposed on the tracing on a video monitor.

A further development in the method of cephalometric evaluation of dental radiographs is also disclosed in a U.S. Pat. No. 5,318,441 of Keller. As disclosed therein, a method for cephalometric evaluation includes steps of generating radiographic, X-ray or other images of a patient's individual orthodontic structure, positioning this image in alignment with a graphical depiction of a norm value orthodontic structure and comparing the individual's structure to the norm value structure to analyze development and to determine a course of orthodontic or other treatment.

Finally, a U.S. Pat. No. 5,342,202 of Deshayes discloses a method for modeling cranio-facial architecture. As disclosed, a process for modeling cranio-facial architecture on the basis of a lateral cephalometric X-ray by determining bony points and plotting analysis lines, measuring the angles and comparing them with thresholds and measuring the lengths and comparing the lengths with one another.

Notwithstanding the above, it is presently believed that there is a need and a potential market for an improved device and method for measuring the skeletodental relationship of a human skull directly from a cephalometric radiograph of the craniofacial structure in accordance with the present invention. There should be a demand for such devices because such devices are believed to facilitate the work of dental students, dentists, orthodontics, and researchers interested in studying dental malocclusions and monitoring the skeletodental relationships of the human craniofacial structures. Such devices should be in demand because they help in measuring the skeletodental relationship of the human skull to study and diagnose dental malocclusions and assess the treatment to be performed. Such devices and methods also help in comparing the changes in the skeletodental relationships after treatments and compare the skeletodental relationships between samples of patients and different populations. It is also presently believed that such devices can be produced at a relatively modest cost and greatly facilitate the work of dentists and orthodontists in evaluating and analyzing the treatments for patients with malocclusions.

BRIEF SUMMARY OF THE INVENTION

A device for measuring the skeletodental relationships of the human skull directly from a cephalometric radiograph or from the hand tracing of the craniofacial structure includes a flat transparent plate-like structure having a generally rectangular shape with a zero point and two protractors superimposed on the zero point and including radial lines from 0° to 90° for a first of the protractors and from 90° to 0° for a second of the protractors and wherein the 0° line in the first protractor is parallel with the 90° in the second protractor and the 90° line in the first protractor is parallel with the 0° line in said second protractor. A vertical scale of normal linear distances on a first edge of the device and a scale of horizontal line dimensions on a second side of the device that is perpendicular to the first side of the device is also included.

The invention will now be described in connection with the accompanying drawings.

DESCRIPTION OF THE PREFERRED EMBODIMENTS OF THE INVENTION

Figure 1:
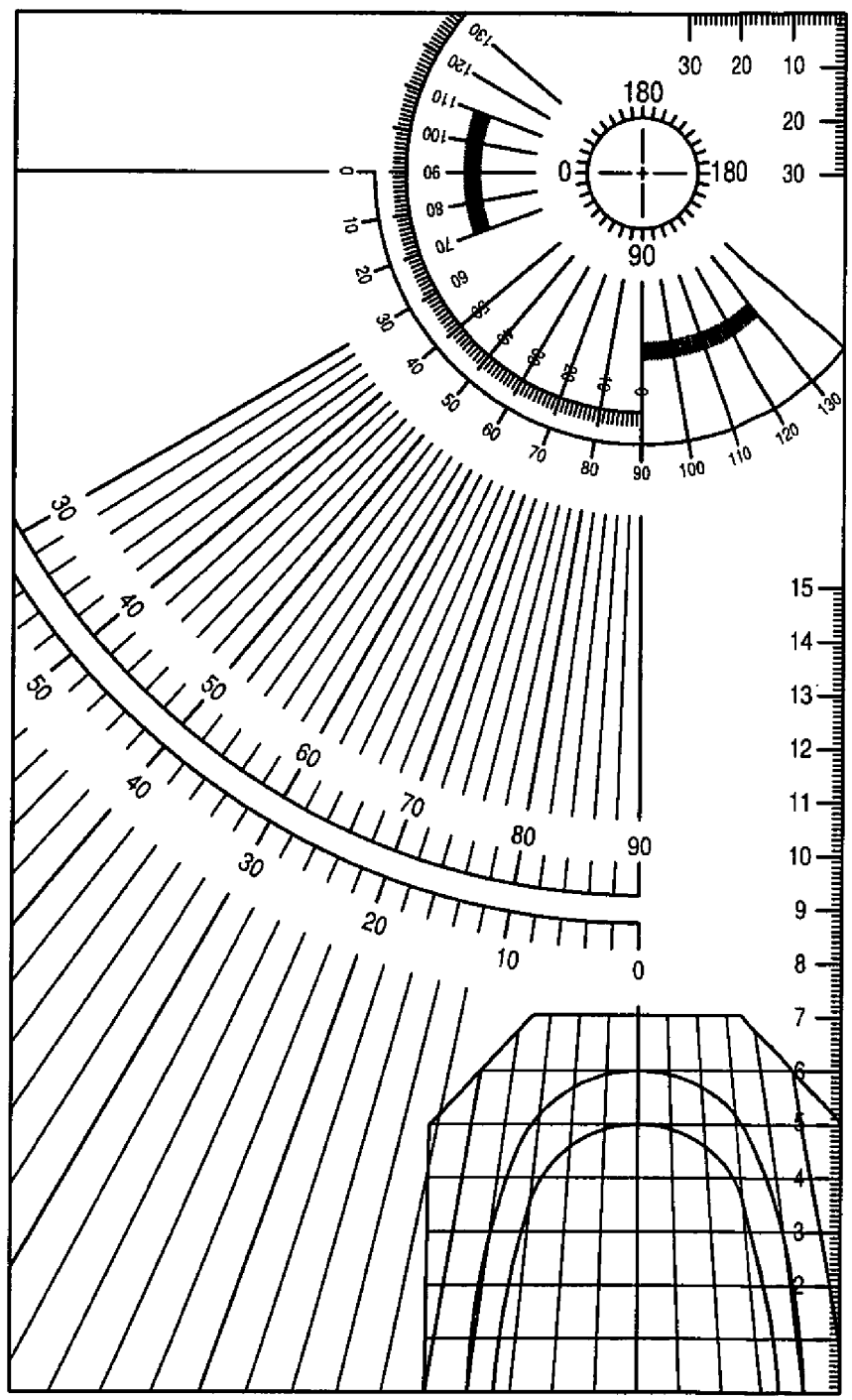
FIG. 1 is a top or plane view of a device in accordance with a first embodiment of the invention.
Figure 2:
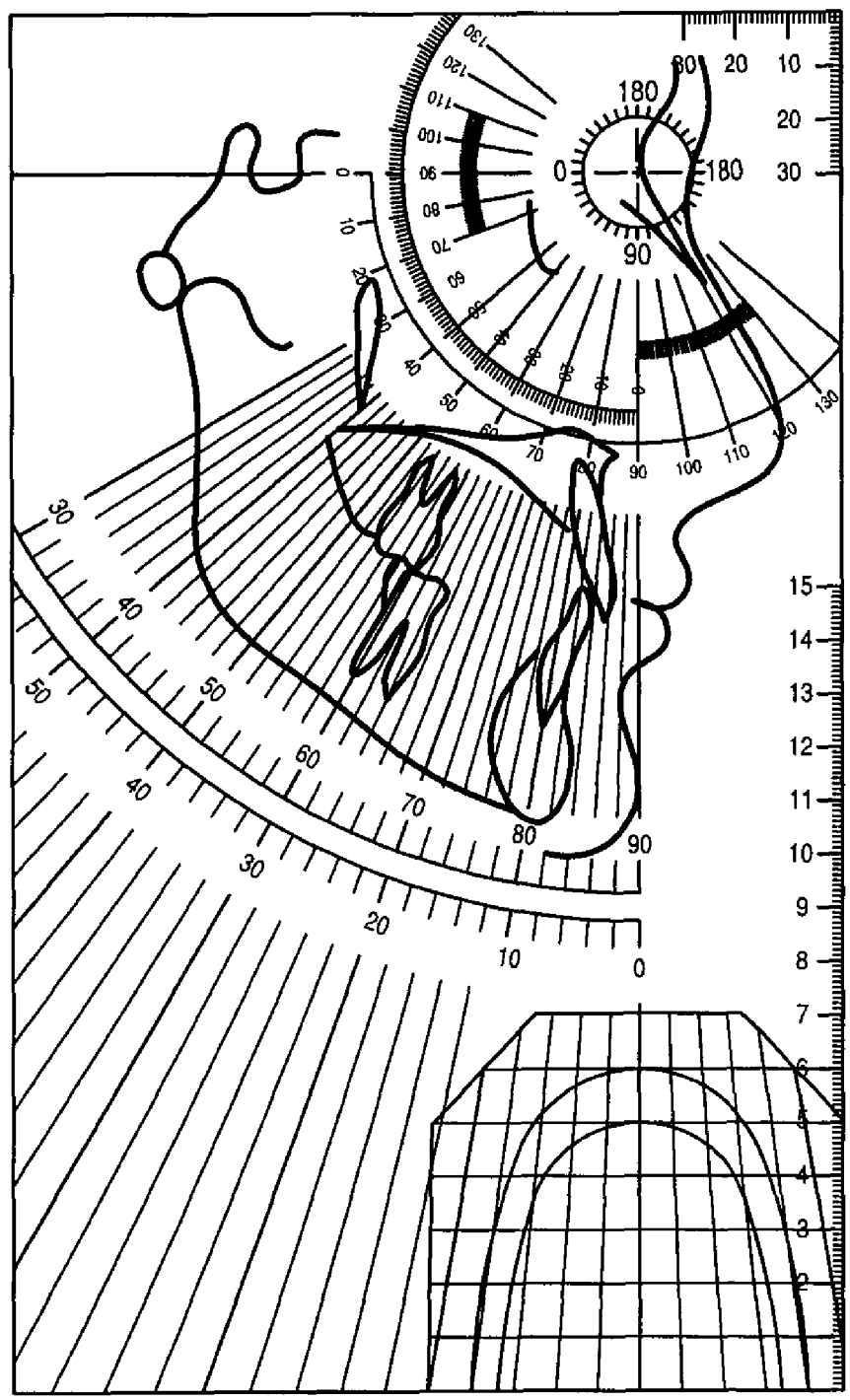
FIG. 2 is a top or plane view of a device in accordance with the invention with a cephalometric radiograph superimposed thereon.
Figure 3:
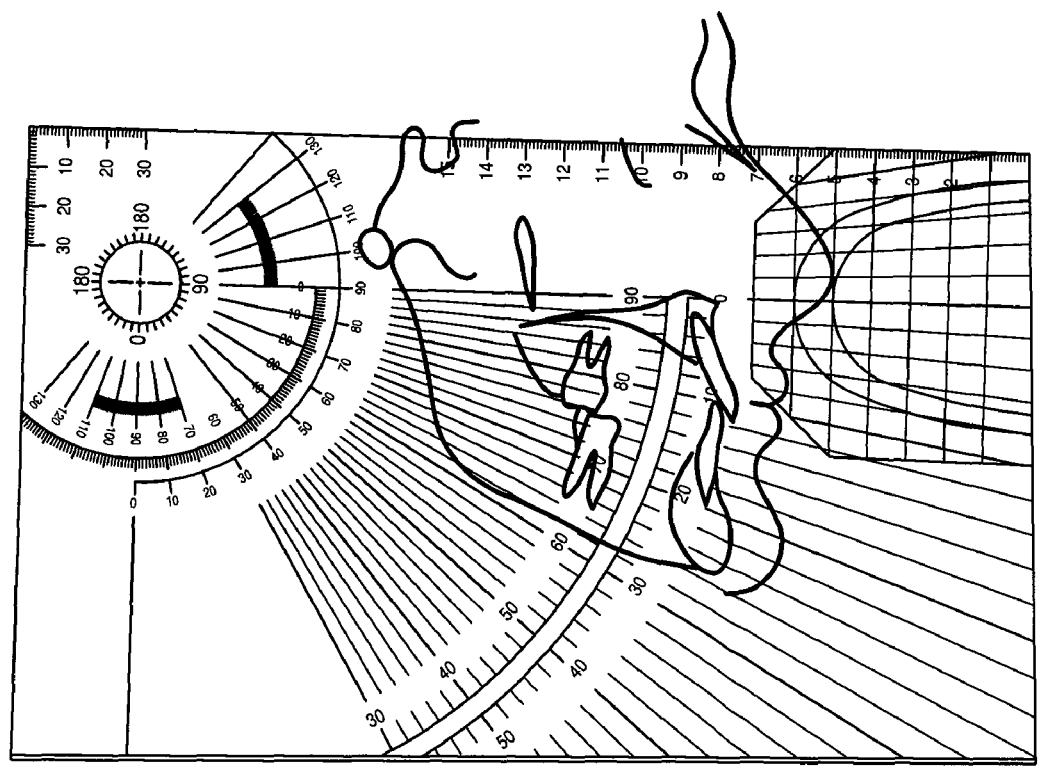
FIG. 3 is a further embodiment of the invention showing a side view of the device with an image of a cephalometric radiograph shown thereon.
Figure 4:
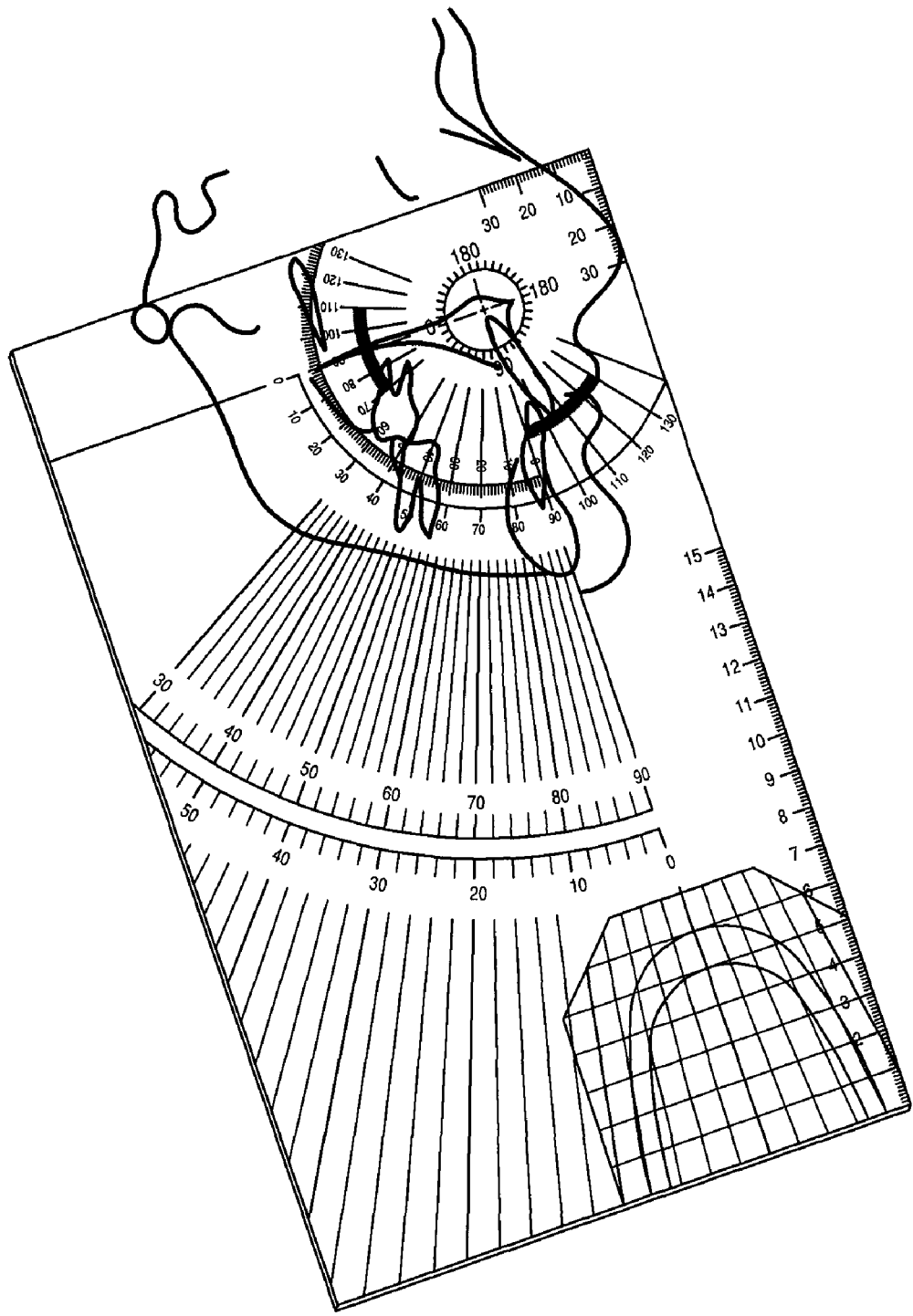
FIG. 4 is a further view of a device in accordance with the invention with a cephalometric radiograph superimposed thereon.
Figure 5:
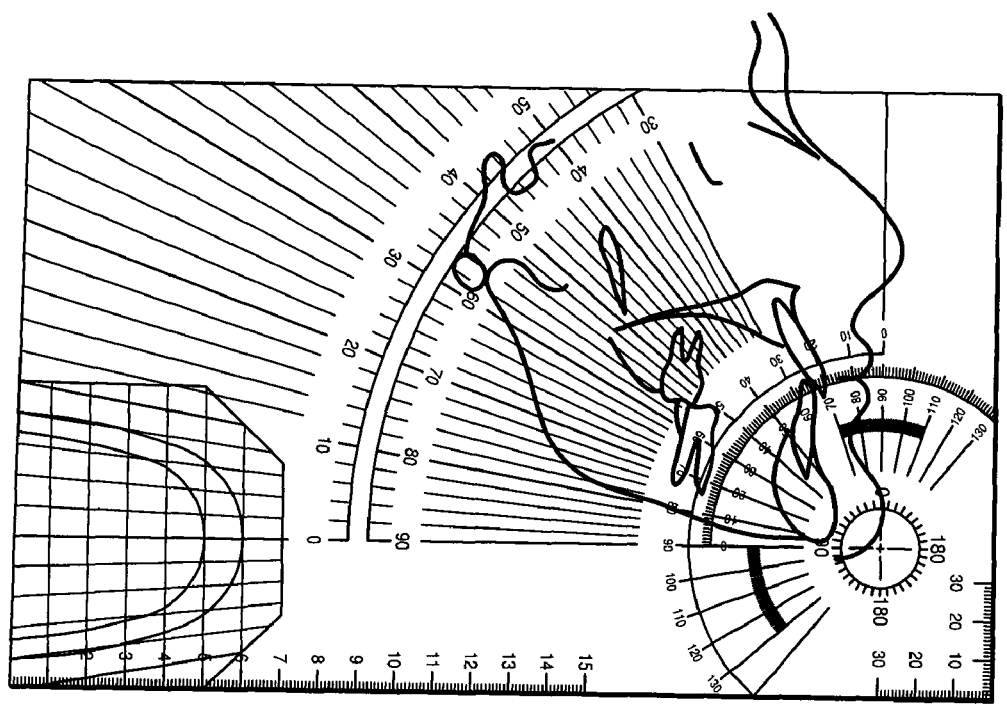
FIG. 5 is a further view of a device in accordance with the invention with a cephalometric radiograph superimposed thereon.

As illustrated in FIG. 1 a device for measuring the skeletodental relationships of a human skull directly from a cephalometric radiograph of the craniofacial structure is illustrated in FIG. 1. As illustrated the device includes a flat transparent plate-like structure having a generally rectangular shape with a zero point and two protractors superimposed on said zero point and including radial lines from 0° to 90° for a first of the protractors and from 90° to 0° for a second of the protractors.

As illustrated, a 0° on the first protractor is parallel with a 90° line on the second protractor and the 90° line on the first protractor is parallel with the 0° line on said second protractor.

In addition a vertical scale of linear distances, as for example millimeters, is provided on a first right hand edge of the device and a scale of horizontal linear dimensions on a second or top side of the device that is perpendicular to the first side. The vertical and horizontal scales are in millimeters while a second rule is provided in a lower part of the vertical edge and provided in centimeters. The transparent structure also includes an image of a dental arch symmetry plus the overall dimensions of the device i.e. about 257 millimeters in length by 160 millimeters in width and about 3 millimeters thick and wherein the zero point is about 40 millimeters distance from the right side of the device and about 30 millimeters from the top. The dental arch is shown in the lower right hand portion of the device.

A device for measuring the skeletodental relationship of a human skull directly from a cephalometric radiograph or from a hand tracing of the craniofacial structure consists of a flat transparent plate-like structure having a rectangular shape with a length of about 257 mm, a width of about 160 mm and a thickness of about 3 mm. The transparent plate-like structure also includes a zero point at about 30 mm from the top and about 40 mm from the right hand side of the device. Two protractors are inscribed or printed on the transparent plate-like structure with a zero point and including radial lines from 0° to 90° for a first of the protractors and from 90° to 0° for a second of the protractors. In addition, the 0° line in said first protractor is parallel to the 90° line in the second protractor and the 90° line in the second protractor is parallel with the 0° line in the first protractor. Further, an image of a dental arch symmetry is provided at a lower right hand portion of the device and includes two arches through which most if not all normal arches would fit. Further, a vertical millimeter scale is provided on an upper right hand edge of the device with a horizontal millimeter scale on an upper edge. Further, a vertical scale is provided on the lower right hand portion of the device adjacent to the dental arches.

A method for measuring the skeletodental relationship of a human skull directly from a cephalometric radiograph of the craniofacial structure includes the steps of providing a device for measuring the skeletodental relationship of a human skull directly from a cephalometric radiograph or from a hand tracing thereof. The method also includes the steps of making a cephalometric radiograph of a patient's skull and placing the radiograph on the device and after placing the radiograph on the device the annular deviations of the radiograph of the skeletodental structure is compared to pre-selected norms and based on the changes, a treatment is prescribed to correct malocclusions.

While the invention has been described in connection with its preferred embodiments it should be recognized that changes and modifications may be made therein without departing from the scope of the appended claims.

What is claimed is:

1. A device for measuring the skeletodental relationship of the human skull directly from a cephalometric radiograph of the craniofacial structure, said device comprising:

a flat transparent plate-like structure having a generally rectangular shape with a length of about 257 mm, a width of about 160 mm and a thickness of about 3 mm, with a zero point and an image of two protractors superimposed on said zero point and including radial lines from 0° to 90° for a first of the protractors and from 90° to 0° for a second of said protractors and wherein said 0° line in said first protractor is parallel to said 90° line in said second protractor and said 90° line in said first protractor is parallel with said 0° line in said second protractor;

and which includes an image of a dental arch symmetry and three scales with a first vertical millimeter scale on an upper right hand edge of the device and a horizontal millimeter scale on an upper edge on the right hand portion and a second vertical scale on a lower right hand portion of the device.

2. A device for measuring the skeletodental relationship of a human skull directly from a cephalometric radiograph of the craniofacial structure according to claim 1 in which the zero point is about 40 mm in distance from the right side of the device and about 30 mm from the top.

3. A device for measuring the skeletodental relationship of a human skull directly from a cephalometric radiograph or from a hand tracing of the craniofacial structure, said device consisting of:

a flat transparent plate-like structure having a rectangular shape with a length of about 257 mm, a width of about 160 mm and a thickness of about 3 mm, and a zero point at about 30 mm from the top and about 40 mm from the right hand side, and two protractors one above the other superimposed on said zero point and including radial lines from 0° to 90° for a first of the protractors and from 90° to 0° for a second of the protractors and wherein said 0° line in said first protractor is parallel to said 90° line in said second protractor and wherein 0° line in said second protractor is parallel with said 90° line in said first protractor;

an image of a dental arch symmetry in a lower right hand portion of said device and three scales with a first vertical millimeter scale on an upper right hand edge of the device and a horizontal millimeter scale on an upper edge on the right hand portion and a second vertical scale on a lower right hand portion of the device.

* * * * *